United States Patent
Kehoe et al.

(10) Patent No.: US 10,377,206 B2
(45) Date of Patent: Aug. 13, 2019

(54) METHODS, APPARATUSES AND COMPUTER PROGRAM PRODUCTS FOR PROVIDING A VENTILATION SYSTEM

(71) Applicant: UNITED PARCEL SERVICE OF AMERICA, INC., Atlanta, GA (US)

(72) Inventors: Michael Patrick Kehoe, Atlanta, GA (US); Robert Joseph D'Ambrosio, Woodstock, GA (US)

(73) Assignee: United Parcel Service of America, Inc., Atlanta, GA (US)

(*) Notice: Subject to any disclaimer, the term of this patent is extended or adjusted under 35 U.S.C. 154(b) by 585 days.

(21) Appl. No.: 14/626,059

(22) Filed: Feb. 19, 2015

(65) Prior Publication Data

US 2015/0231945 A1   Aug. 20, 2015

Related U.S. Application Data

(60) Provisional application No. 61/941,648, filed on Feb. 19, 2014.

(51) Int. Cl.
*B60H 1/00* (2006.01)
*G01N 33/00* (2006.01)
(Continued)

(52) U.S. Cl.
CPC .............. *B60H 1/008* (2013.01); *B60H 1/241* (2013.01); *G01N 33/0047* (2013.01); *G01N 33/0063* (2013.01)

(58) Field of Classification Search
CPC .............. B60H 1/0025; B60H 1/00257; G01N 33/0047; G01N 33/0036; G01N 33/0063; B65D 88/74; B65D 88/741; B65D 88/745
See application file for complete search history.

(56) References Cited

U.S. PATENT DOCUMENTS

| 4,450,900 A | * | 5/1984 | Nathan | ............... B60H 1/00257 165/42 |
| 6,895,764 B2 | * | 5/2005 | Viegas | ............... B60H 1/00257 62/237 |

(Continued)

OTHER PUBLICATIONS

ChemDAQ, Jan. 13, 2014, "Combustible and Toxic Gas Sensors for Ethylene Oxide", http://www.chemdaq.com/combustible-and-toxic-gas-sensors-for-ethylene-oxide/.*

*Primary Examiner* — Gregory L Huson
*Assistant Examiner* — Elizabeth M. May
(74) *Attorney, Agent, or Firm* — Shook, Hardy & Bacon L.L.P.

(57) ABSTRACT

An apparatus is provided for removing gas from a vehicle storage unit. The apparatus includes at least one memory and a processor(s) detecting air being drawn, via an exhaust unit, from the front of a vehicle storage space to a rear of the vehicle storage space and through a ventilation unit forcing the air including emitted gas(es) to exit a top of the ventilation unit. The air is initially directed, from a supply unit in an upper part of the ventilation unit, into the rear of the vehicle storage space to the front of the vehicle storage space. The items emitted the gas. The computer program code may further cause the apparatus to measure the gas as the air passes through the ventilation unit to determine whether the measured gas equals or is below a predetermined threshold. Corresponding computer program products and methods are also provided.

18 Claims, 14 Drawing Sheets

(51) Int. Cl.
*B60H 1/26* (2006.01)
*B60P 3/00* (2006.01)
*B60H 1/24* (2006.01)

(56) References Cited

U.S. PATENT DOCUMENTS

| | | | | |
|---|---|---|---|---|
| 7,171,312 | B2* | 1/2007 | Steinthal | B82Y 30/00 422/82.02 |
| 7,908,791 | B1* | 3/2011 | Brash | A01M 13/003 43/125 |
| 8,177,883 | B2* | 5/2012 | Jorgensen | B65D 81/2076 422/3 |
| 2009/0272024 | A1* | 11/2009 | Rogacki | A01M 13/003 43/125 |
| 2011/0146311 | A1* | 6/2011 | Thogersen | F25B 39/028 62/115 |
| 2011/0233068 | A1* | 9/2011 | Warburton | B01D 53/04 205/554 |
| 2011/0281367 | A1* | 11/2011 | Walte | G01N 33/0013 436/93 |
| 2015/0032266 | A1* | 1/2015 | Weast | B60H 1/008 700/276 |
| 2016/0272048 | A1* | 9/2016 | Casasanta | B60L 1/003 |

* cited by examiner

METHODS, APPARATUSES AND COMPUTER PROGRAM PRODUCTS FOR PROVIDING A VENTILATION SYSTEM

CROSS-REFERENCE TO RELATED APPLICATIONS

This application claims priority to and the benefit of U.S. Provisional Patent Application Ser. No. 61/941,648, filed Feb. 19, 2014, the contents of which are hereby incorporated by reference in their entirety.

TECHNOLOGICAL FIELD

Embodiments of the invention relate generally to safely and efficiently exhausting air from a storage space of a vehicle that may have high levels of gas such as, for example, Ethylene Oxide (EtO) upon arriving at a facility and more generally relate to methods, apparatuses and computer program products for maintaining gas (e.g., EtO) levels at or below an acceptable threshold.

BACKGROUND

Transportation vehicles often transport items that include hazardous or harmful gases. For example, Ethylene Oxide ("EtO") is commonly used to sterilize medical equipment that is transported by carriers such as United Parcel Service of America, Inc. EtO is hazardous, combustible, and heavier than air. Products sterilized with EtO and being transported by a carrier may continue to off-gas EtO during transport. As such, personnel (e.g., drivers, loaders, etc.) of carriers may be exposed to this EtO gas.

Exposure above certain limits to EtO may create health risks for individuals. For instance, EtO is a carcinogen that may cause cancer as well as other health issues (e.g., genetic damage, nerve damage, peripheral paralysis, impaired thinking, etc.). In fact, Occupational Safety and Health Administration (OSHA) has established guidelines for exposure to EtO. Accordingly, companies seek to limit exposure to EtO to meet the OSHA guidelines.

Therefore, a need may exist for monitoring and removal of hazardous or harmful gases from transport vehicles in an efficient and reliable manner to reduce user exposure to harmful gases.

BRIEF SUMMARY

A method, apparatus and computer program product are therefore provided for enabling a ventilation system to quickly, safely, and efficiently exhaust air from a vehicle storage unit (e.g., a trailer) of a vehicle with potentially high levels of gas(es) such as, for example, EtO gas upon arriving at various facilities.

In this regard, an exemplary embodiment may provide air monitoring techniques to remove a gas(es) (e.g., EtO gas) from transport vehicles and detect whether gas(es)) (e.g., EtO gas) levels are below certain thresholds in order to maintain the gas(es) (e.g., EtO gas) at safe and acceptable levels without requiring user interaction to manually take measurements of the gas(es) (e.g., EtO gas).

For example, a ventilation system (also referred to herein as ventilation unit) of an exemplary embodiment, may blow, via one or more fans/blowers, a high-velocity jet of air between the top of one or more items (e.g., products, packages, etc.) and a ceiling of a storage space/area (e.g., a trailer) of a vehicle. In some example embodiments, the high velocity jet of air may reach the front of a long storage space area (e.g., a 53 feet long trailer). At the front of the storage space/area (e.g., trailer), the air may slow down, and return to the rear/back of the storage space/area (e.g., trailer) of the vehicle. On the return path to the rear/back of the storage space/area (e.g., trailer), the air may move between and under other items (e.g., pallets, packages, etc.), and may exhaust gas (e.g., EtO gas) in the storage space/area with the air by utilizing one or more exhaust fans.

The ventilation system may include a gas detection device (also referred to herein as a gas detection module) to measure the gas levels (EtO levels) of air being exhausted from the storage space area (e.g., trailer) of a vehicle. This eliminates a need for personnel of a carrier to enter the storage space area (e.g., trailer) to manually measure gas levels (e.g., EtO levels). In an example embodiment, the ventilation system may be run or implemented until the gas detection module measures/detects that gas (e.g., EtO) in the storage space area (e.g., trailer) reaches a target level (e.g., a predetermined threshold) or a level lower than the target level.

In one example embodiment, a method for removing gas from a vehicle storage unit is provided. The method may include directing a stream of air, proximate an upper part of a vehicle storage space between one or more items and a ceiling of the vehicle storage space, via an air supply unit. The method may further include drawing air via an exhaust unit from a front of the vehicle storage space to a rear of the vehicle storage space and through a ventilation unit forcing the air comprising at least one emitted gas to exit out of a top portion of the ventilation unit. The method may further include measuring the emitted gas as the drawn air passes through the ventilation unit to determine whether the measured gas equals or is below a predetermined threshold.

In another example embodiment, an apparatus for removing gas from a vehicle storage unit is provided. The apparatus may include a processor and a memory including computer program code. The memory and the computer program code are configured to, with the processor, cause the apparatus to at least perform operations including detecting air being drawn, via an exhaust unit, from the front of a vehicle storage space to a rear of the vehicle storage space and through a ventilation unit forcing the air including at least one emitted gas to exit out of a top portion of the ventilation unit. The air is initially directed, from a supply unit located in an upper part of the ventilation unit, into the rear of the vehicle storage space, between an upper portion of one or more items and a ceiling of the vehicle storage space, to the front of the vehicle storage space. The items emitted the gas. The memory and the computer program code are further configured to, with the processor, cause the apparatus to measure the emitted gas as the drawn air passes through the ventilation unit to determine whether the measured gas equals or is below a predetermined threshold.

In another example embodiment, a ventilation unit for removing gas from a vehicle storage unit is provided. The ventilation unit includes a supply unit located in an upper part of the ventilation unit. The supply unit is configured to direct a stream of air from a rear of a vehicle storage space, between an upper portion of one or more items and a ceiling of the vehicle storage space, to a front of the vehicle storage space. The items emit at least one gas. The ventilation unit also includes an exhaust unit located in a lower part of the ventilation unit. The exhaust unit is configured to draw the air, including the emitted gas, from the front of the vehicle storage space to the rear of the vehicle storage space and through the ventilation unit forcing the air including the emitted gas to exit out of a top portion of the ventilation unit. The ventilation unit also includes a gas detection device configured to measure the gas as the drawn air passes through the ventilation unit. The gas detection device is configured to determine whether the measured gas equals or is below a predetermined threshold.

BRIEF DESCRIPTION OF THE SEVERAL VIEWS OF THE DRAWINGS

Figure 1:
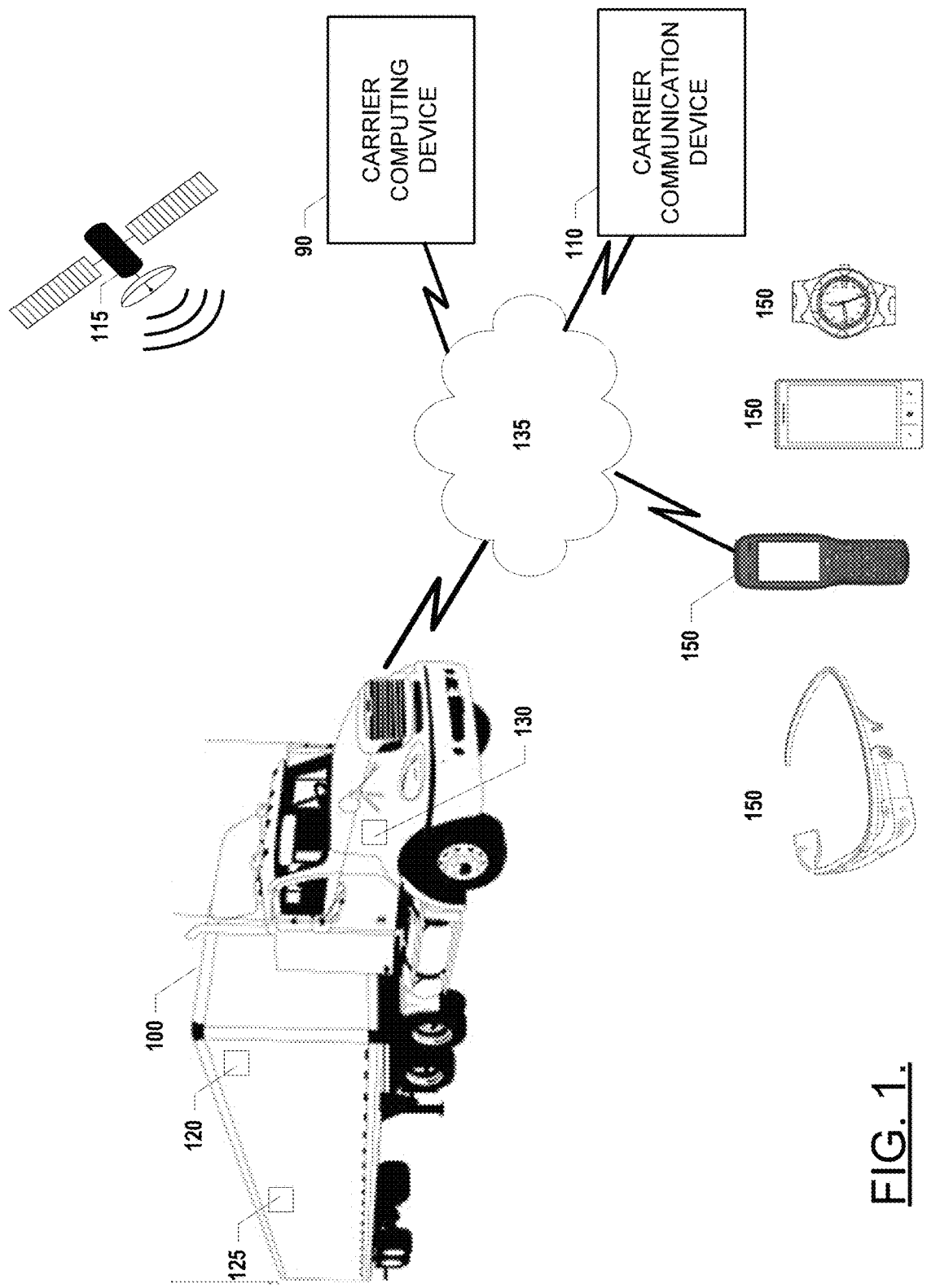
Figure 2:
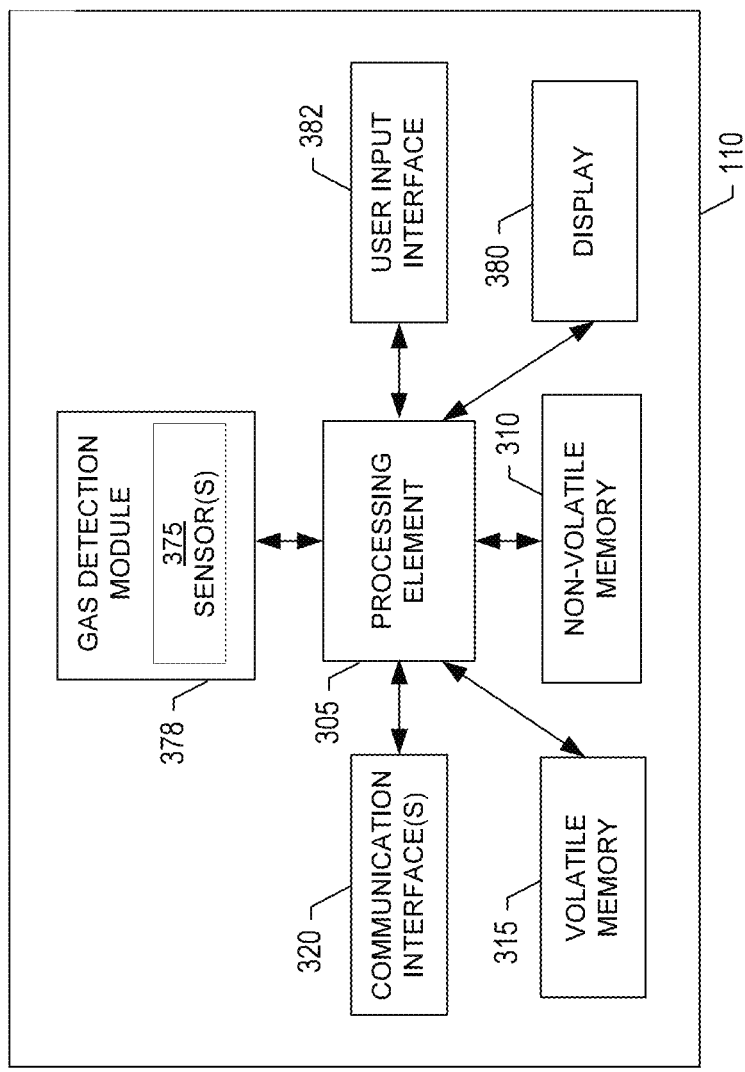
Figure 3:
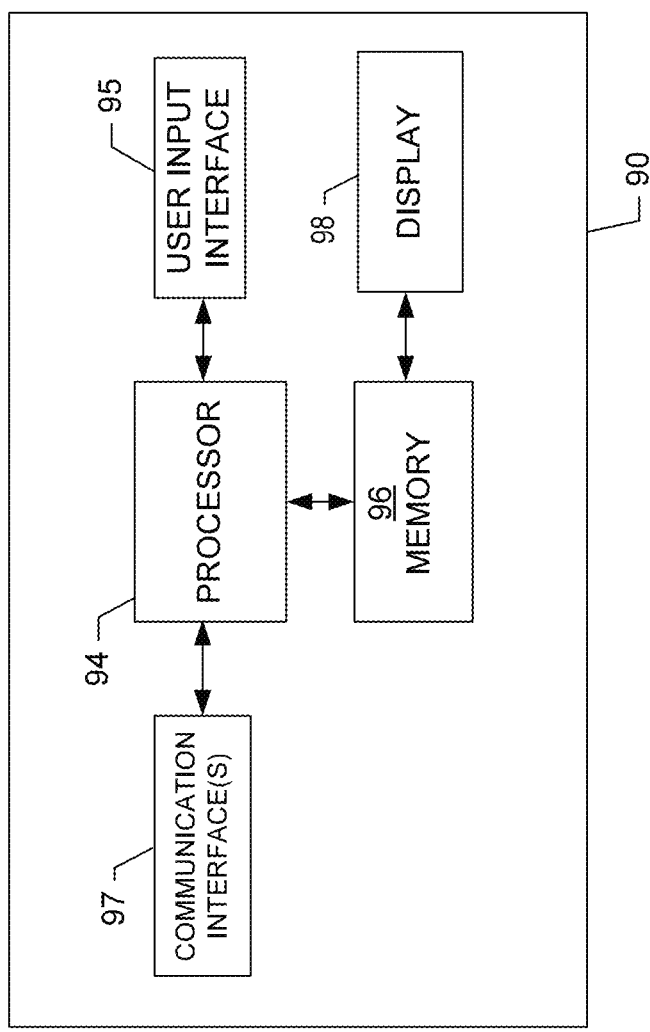
Figure 4:
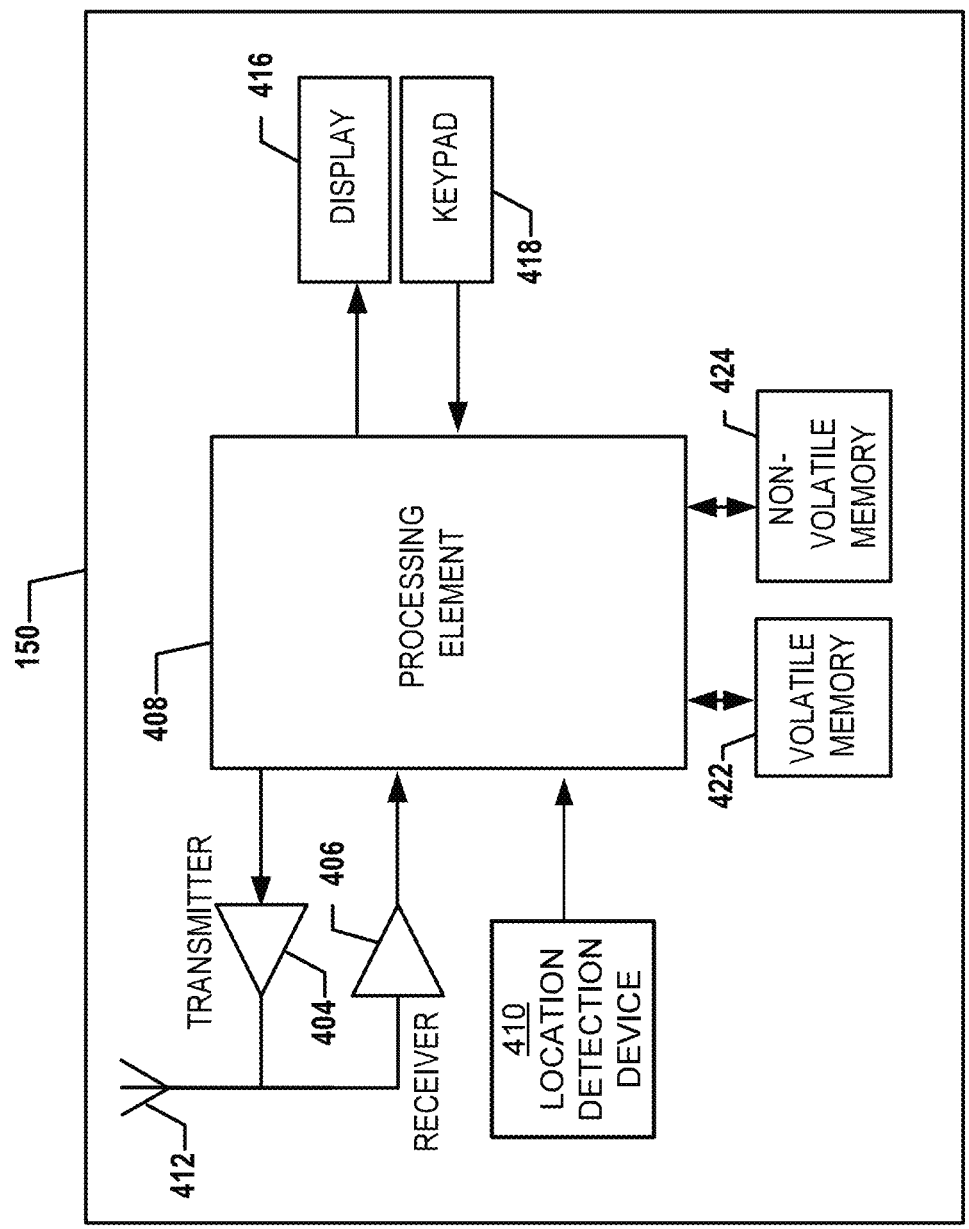
Figure 5A:
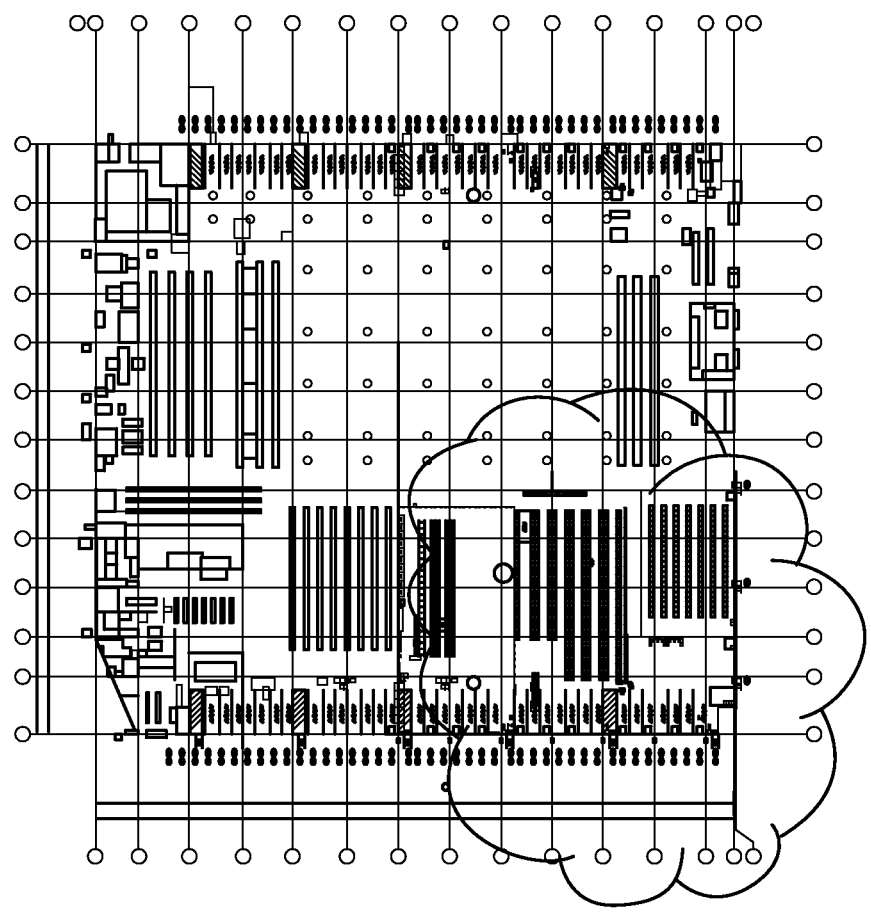
Figure 5B:
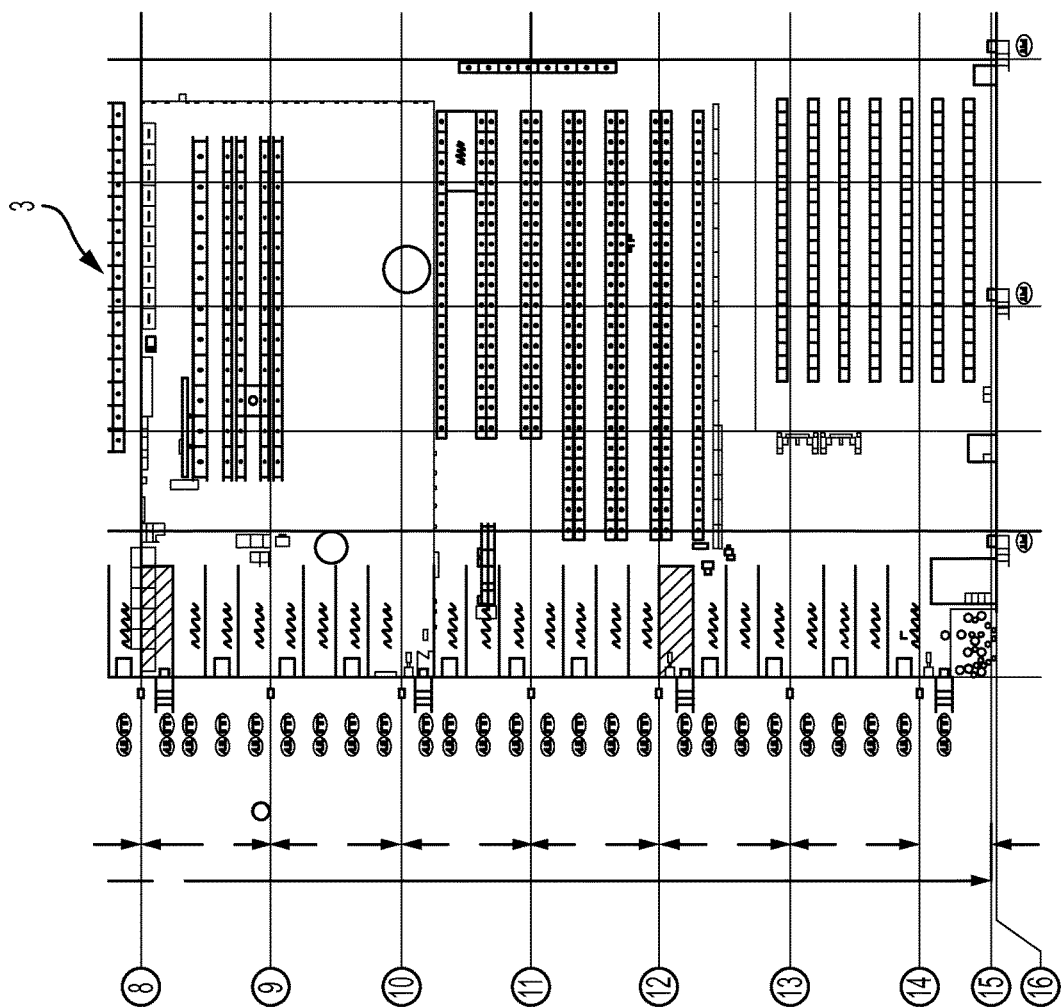
Figure 10:
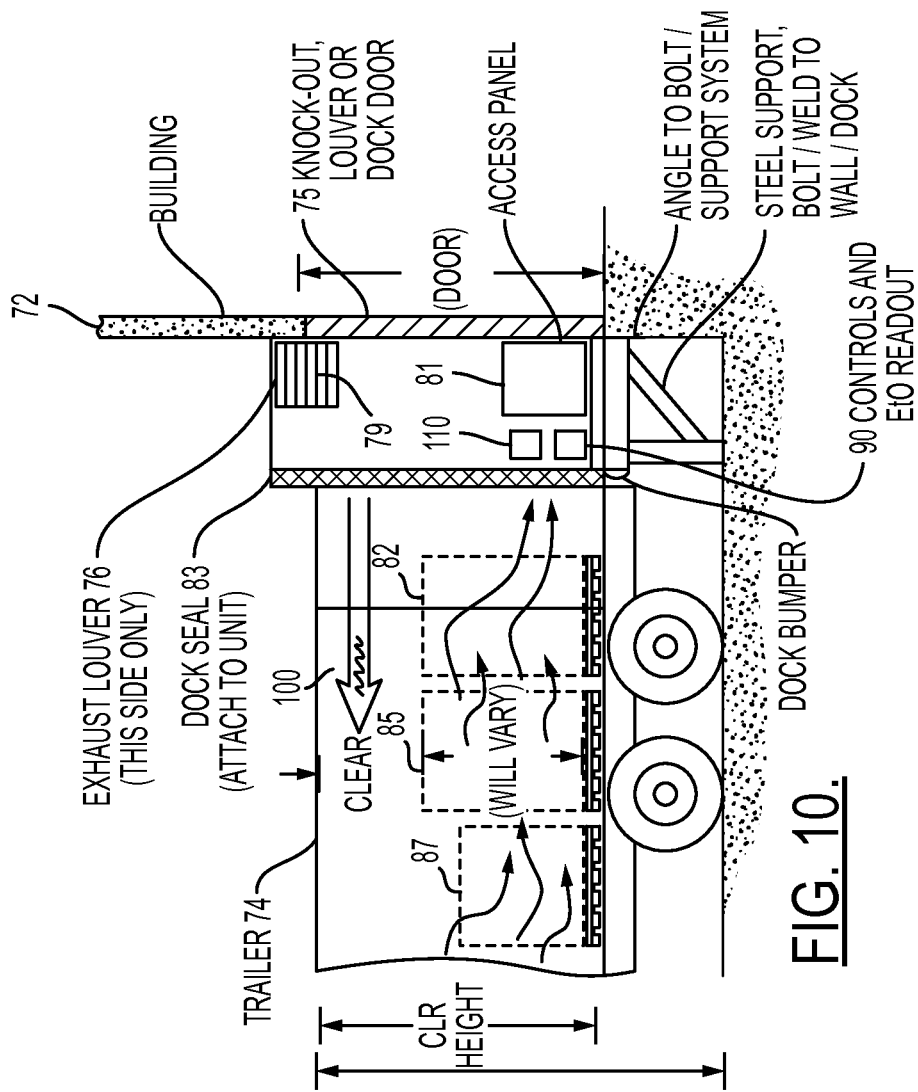
Figure 11:
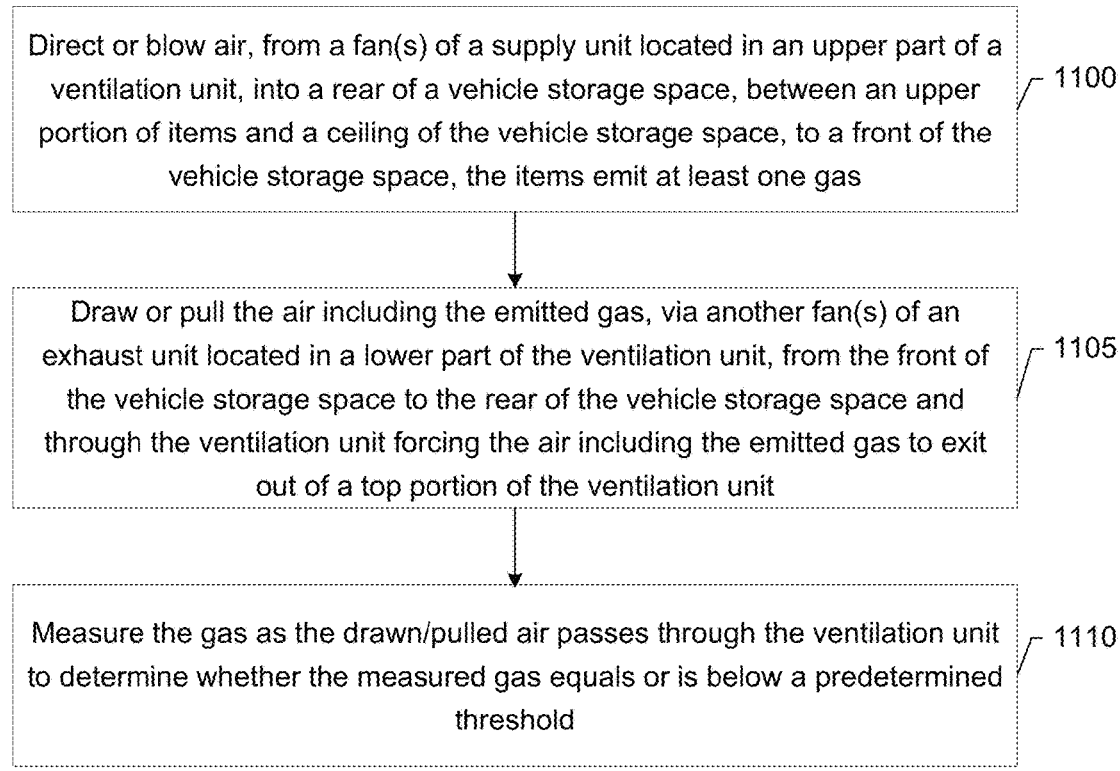
Figure 12:
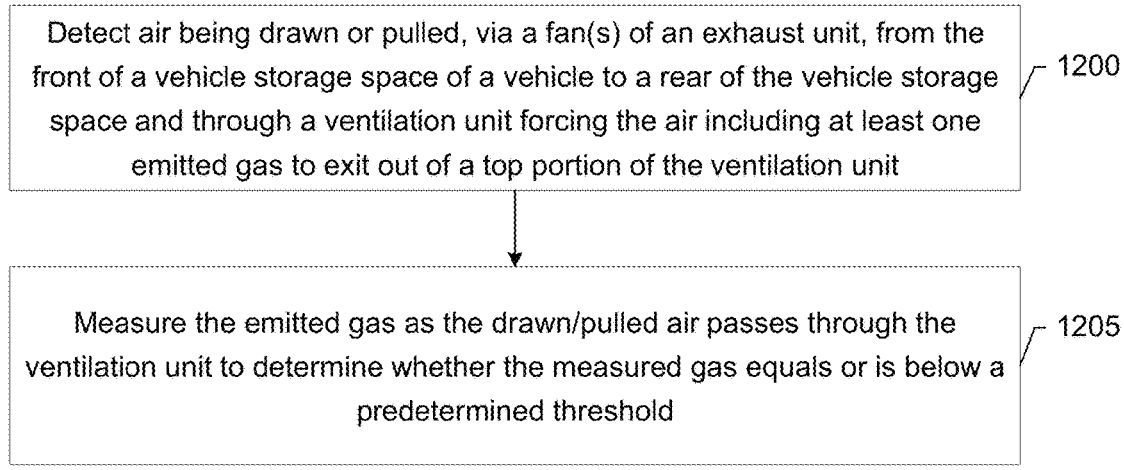

Having thus described the invention in general terms, reference will now be made to the accompanying drawings, which are not necessarily drawn to scale, and wherein:

FIG. 1 is a diagram of a system that can be used to practice various embodiments of the invention;

FIG. 2 is a diagram of a carrier communication device that may be used in association with certain embodiments of the invention;

FIG. 3 is a diagram of a computing device in accordance with certain embodiments of the invention;

FIG. 4 is a diagram of a mobile device in accordance with certain embodiments of the invention;

FIG. 5A and FIG. 5B illustrate an exemplary layout of a facility in accordance with an example embodiment of the invention;

FIG. 6A, FIG. 6B, FIG. 6C, FIG. 6D, FIG. 7, FIG. 8 and FIG. 9 illustrate exemplary ventilation systems in accordance with various embodiments of the invention;

FIG. 10 is a diagram illustrating a ventilation system in a facility according to an example embodiment of the invention;

FIG. 11 illustrates a flowchart for removing gas from a vehicle storage unit according to an example embodiment of the invention; and FIG. 12 illustrates a flowchart for removing gas from a vehicle storage unit according to another example embodiment of the invention.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

As defined herein, a computer-readable storage medium," which refers to a non-transitory, physical or tangible storage medium (e.g., volatile or non-volatile memory device), may be differentiated from a "computer-readable transmission medium," which refers to an electromagnetic signal.

I. Exemplary System Architecture

FIG. 1 provides an illustration of a system that can be used in conjunction with various embodiments of the present invention. As shown in FIG. 1, the system may include one or more vehicles 100, one or more mobile devices 150, one or more carrier communication devices 110, one or more carrier computing devices 90, one or more Global Positioning System (GPS) satellites 115, one or more location sensors 120, one or more telematics sensors 125, one or more data collection devices 130, one or more networks 135, and/or the like. Each of the components of the system may be in electronic communication with, for example, one another over the same or different wireless or wired networks including, for example, a wired or wireless Personal Area Network (PAN), Local Area Network (LAN), Metropolitan Area Network (MAN), Wide Area Network (WAN), or the like. Additionally, while FIG. 1 illustrates certain system entities as separate, standalone entities, the various embodiments are not limited to this particular architecture.

a. Exemplary Vehicle

In various embodiments, the term vehicle 100 is used generically. For example, a vehicle 100 may be a trailer, a tractor, a tractor and trailer combination (also referred to herein as tractor-trailer), a van, a truck, a car, a vehicle, similar words used herein interchangeably, and/or any other form of object for moving or transporting people and/or items (e.g., one or more packages, parcels, bags, containers, loads, crates, items banded together, vehicle parts, pallets, drums, the like, and/or similar words used herein interchangeably). Although in certain embodiments, the vehicle may be unmanned. In one embodiment, each vehicle 100 may be associated with a unique vehicle identifier (such as a vehicle ID) that uniquely identifies the vehicle 100. The unique vehicle ID (e.g., trailer ID, tractor ID, vehicle ID, and/or the like) may include characters, such as numbers, letters, symbols, and/or the like. For example, an alphanumeric vehicle ID (e.g., "AS445") may be associated with each vehicle 100. In another embodiment, the unique vehicle ID may be the license plate, registration number, or other identifying information assigned to the vehicle 100.

FIG. 1 shows one or more computing entities, devices, and/or similar words used herein interchangeably that are associated with the vehicle 100, such as a data collection device 130 or other computing entities. In general, the terms computing entity, entity, device, system, and/or similar words used herein interchangeably may refer to, for example, one or more computers, computing entities, mobile phones, desktops, tablets, notebooks, laptops, distributed systems, gaming consoles (e.g., Xbox, Play Station, Wii), watches, televisions, dongles, glasses, key fobs, radio frequency identification (RFID) tags, ear pieces, scanners, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein.

b. Exemplary Carrier Communication Device

FIG. 2 provides a schematic of a carrier communication device 110 according to an example embodiment. In general, the term communication device may refer to, for example, one or more computers, computing devices, computing entities, mobile phones, desktops, tablets, notebooks, laptops, distributed systems, servers, network devices, blades, gateways, switches, processing devices, processing entities, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the carrier communication device 110 may also include one or more communications interfaces 320 for communicating with various computing entities, such as by communicating data, content, information, and/or similar terms used herein interchangeably that can be transmitted, received, operated on, processed, displayed (e.g., via display 380), stored, and/or the like. For instance, the carrier communication device 110 may communicate with vehicles 100, carrier computing devices 90, mobile devices 150, and/or the like.

As shown in FIG. 2, in one embodiment, the carrier communication device 110 may include or be in communication with one or more processing elements 305 (also referred to as processors, processing circuitry, and/or similar terms used herein interchangeably) that communicate with other elements within the carrier communication device 110 via a bus, for example. As will be understood, the processing element 305 may be embodied in a number of different ways. For example, the processing element 305 may be embodied as one or more complex programmable logic devices (CPLDs), microprocessors, multi-core processors, coprocessing entities, application-specific instruction-set processors (ASIPs), and/or controllers. Further, the processing element 305 may be embodied as one or more other processing devices or circuitry. The term circuitry may refer to an entirely hardware embodiment or a combination of hardware and computer program products. Thus, the processing element 305 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 305 may be configured for a particular use or configured to execute instructions stored in volatile or non-volatile media or otherwise accessible to the processing element 305. As such, whether configured by hardware or computer program products, or by a combination thereof, the processing element 305 may be capable of performing steps or operations according to embodiments of the present invention when configured accordingly.

In one example embodiment, the carrier communication device 110 may further include or be in communication with non-volatile memory 310 (also referred to as non-volatile storage, memory, memory storage, memory circuitry and/or similar terms used herein interchangeably). In one embodiment, the non-volatile storage or memory may include one or more non-volatile storage or memory media as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database carrier systems, information/data, applications, programs, program modules, scripts, source code, object code, byte code, compiled code, interpreted code, machine code, executable instructions, and/or the like. The term database, database instance, database carrier system, and/or similar terms used herein interchangeably may refer to a structured collection of records or information/data that is stored in a computer-readable storage medium, such as via a relational database, hierarchical database, and/or network database.

In one example embodiment, the carrier communication device 110 may further include or be in communication with volatile memory 315 (also referred to as volatile storage, memory, memory storage, memory circuitry and/or similar terms used herein interchangeably). In one example embodiment, the volatile memory 315 may also include one or more volatile storage or memory media as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database carrier systems, information/data, applications, programs, program modules, scripts, source code, object code, byte code, compiled code, interpreted code, machine code, executable instructions, and/or the like being executed by, for example, the processing element 305. Thus, the databases, database instances, database carrier systems, information/data, applications, programs, program modules, scripts, source code, object code, byte code, compiled code, interpreted code, machine code, executable instructions, and/or the like may be used to control certain aspects of the operation of the carrier communication device 110 with the assistance of the processing element 305 and operating system.

As indicated, in one example embodiment, the carrier communication device 110 may also include one or more communications interfaces 320 for communicating with various computing entities, such as by communicating information/data, content, information, and/or similar terms used herein interchangeably that can be transmitted, received, operated on, processed, displayed, stored, and/or the like. For instance, the carrier communication device 110 may communicate with computing entities or communication interfaces of the vehicle 100 (e.g., tractor, trailer, tractor and/or trailer, delivery vehicle), mobile devices 150, and/or the like.

Such communication may be executed using a wired information/data transmission protocol, such as fiber distributed information/data interface (FDDI), digital subscriber line (DSL), Ethernet, asynchronous transfer mode (ATM), frame relay, information/data over cable service interface specification (DOCSIS), or any other wired transmission protocol. Similarly, the carrier communication device 110 may be configured to communicate via wireless external communication networks using any of a variety of protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol. Although not shown, the carrier communication device 110 may include or be in communication with one or more input elements, such as a keyboard input, a mouse input, a touch screen/display input, audio input, pointing device input, joystick input, keypad input, and/or the like. The carrier communication device 110 may also include or be in communication with one or more output elements (not shown), such as audio output, video output, screen/display output, motion output, movement output, and/or the like.

In addition to the communication interface(s), the interface(s) may also include at least one user interface that may include one or more earphones and/or speakers, a display 380, and/or a user input interface 382. The user input interface, in turn, may comprise any of a number of devices allowing the carrier communication device to receive data from a user, such as a microphone, a keypad, keyboard, a touch display, a joystick, image capture device, pointing device (e.g., mouse), stylus or other input device.

As will be appreciated, one or more of the components of the carrier communication device 110 may be located remotely from other components of the carrier communication device 110, such as in a distributed system. Furthermore, one or more of the components may be combined and additional components performing functions described herein may be included in the carrier communication device 110. Thus, the carrier communication device 110 may be adapted to accommodate a variety of needs and circumstances.

In an exemplary embodiment, the processing element 305 may be in communication with and may otherwise control a gas detection module 378. The gas detection module 378 may be any means such as a device or circuitry operating in accordance with software or otherwise embodied in hardware or a combination of hardware and software thereby configuring the device or circuitry (e.g., a processor, controller, microprocessor or the like) to perform the corresponding functions of the gas detection module 378, as described below. In one example embodiment, the gas detection module may, but need not, be employed in a special purpose chip such as, for example, an application-specific integrated circuit (ASIC) or a field-programmable gate array (FPGA). In examples in which software is employed, a device or circuitry (e.g., processing element 305 in one example) executing the software forms the structure associated with such means. As such, for example, the gas detection module 378 may be configured to, among other things, continuously, or periodically sample exhaust air in a ventilation system (e.g., ventilation system 70 of FIGS. 6A-6D) to determine/measure the levels of EtO as well as other gases (e.g., carbon monoxide (CO), nitrogen oxides (NOx), sulfer oxides (SOx), ozone ($O_3$), hydrogen sulfide ($H_2S$) and/or ammonium, etc.) in the exhaust air. For instance, the gas detection module 378 (also referred to herein as gas detection sensor 378) may include one or more sensors 375 that detect and measure the concentration of one or more gases, as described more fully below. Additionally, the gas detection module 378 may send the detected measurements to a mobile device (e.g., mobile device 150) and/or a computing device (e.g., computing device 90) which may be mounted on a side of the ventilation system for viewing by a user indicating EtO levels in a storage area (e.g., a trailer) of a transport vehicle (e.g., vehicle 100 (e.g., a tractor-trailer)), as described more fully below.

c. Exemplary Carrier Computing Device

Referring now to FIG. 3, a block diagram of an example embodiment of a carrier computing device is provided. As shown in FIG. 3, the carrier computing device 90 (also referred to herein as a controls and EtO readout device 90 or a computing device 90) (e.g., a server) generally includes a processor 94 and an associated memory 96. The memory 96 may comprise volatile and/or non-volatile memory, and may store content, data and/or the like. The memory 96 may store client applications, instructions, and/or the like for the processor 94 to perform the various operations of the computing device 90. In addition, the memory 96 may store one or more gas measurements such as, for example, measurements of EtO, etc. The computing device 90 may also include a display 98. In an example embodiment, the display 98 may show one or more gas readings, such as, for example, one or more detected EtO measurements. In one exemplary embodiment, the computing device 90 may be mounted on a side of a ventilation system (e.g., ventilation system 70 of FIGS. 6A-6D). In this manner, one or more EtO measurements may be displayed via display 98 from the side in which the computing device is mounted to the ventilation system. In another exemplary embodiment, the computing device 90 may be external (e.g., located externally) to the ventilation system (e.g., ventilation system 70 of FIGS. 6A-6D). As such, a user (e.g., personnel of a carrier) may view one or more detected gas measurements (e.g., EtO measurements, etc.) shown via display 98 without the user having to enter the ventilation system (e.g., ventilation system 70 of FIGS. 6A-6D) to obtain (e.g., manually obtain) or view a gas measurement(s) (e.g., EtO measurements, etc.), as described more fully below.

The processor 94 may also be connected to at least one communication interface 97 or other means for displaying, transmitting and/or receiving data, content, and/or the like. The user input interface 95 may comprise any of a number of devices allowing the computing device 90 to receive data from a user, such as a keypad, a touch display, a joystick or other input device. In this regard, the processor 94 may comprise user interface circuitry configured to control at least some functions of one or more elements of the user input interface. The processor 94 and/or user interface circuitry of the processor may be configured to control one or more functions of one or more elements of the user interface through computer program instructions (e.g., software and/or firmware) stored on a memory accessible to the processor (e.g., volatile memory, non-volatile memory, and/or the like).

The computing device 90 may receive one or more detected gas measurements (e.g., EtO measurements, etc.) from the gas detection module 378 of the carrier communication device 110.

d. Exemplary Mobile Device

FIG. 4 provides an illustrative schematic representative of a mobile device 150 that may be used in conjunction with embodiments of the present invention. In one embodiment, the mobile devices 150 may include one or more components that are functionally similar to those of the carrier communication device 110 and/or as described below. As will be recognized, mobile devices 105 may be operated by various parties, including operators of vehicles 100 as well as other personnel (e.g., loaders, sorters, etc.) of a carrier. As shown in FIG. 4, a mobile device 150 may include an antenna 412, a transmitter 404 (e.g., a radio), a receiver 406 (e.g., a radio), and a processing element 408 that provides signals to and receives signals from the transmitter 404 and receiver 406, respectively.

The signals provided to and received from the transmitter 404 and the receiver 406, respectively, may include signaling data in accordance with an air interface standard of applicable wireless systems to communicate with various entities, such as vehicles 100, carrier communication entities 110, and/or the like. In this regard, the mobile device 150 may be capable of operating with one or more air interface standards, communication protocols, modulation types, and access types. More particularly, the mobile device 150 may operate in accordance with any of a number of wireless communication standards and protocols. In a particular embodiment, the mobile device 105 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the mobile device 150 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The mobile device 150 may also download changes, add-ons, and updates, for instance, to its firmware, software (e.g., including executable instructions, applications, program modules), and operating system.

According to one embodiment, the mobile device 150 may include location determining aspects, devices, modules, functionalities, and/or similar words used herein interchangeably. For example, the mobile device 150 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information may be determined by triangulating the mobile device's 150 position in connection with a variety of other systems, including cellular towers, Wi-Fi access points, and/or the like. Similarly, the mobile device 150 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The mobile device 150 may also comprise a user interface (that can include a display 416 coupled to a processing element 408) and/or a user input interface (coupled to a processing element 408). For example, the user interface may be an application, browser, user interface, dashboard, webpage, and/or similar words used herein interchangeably executing on and/or accessible via the mobile device 150 to interact with and/or cause display of information. The user input interface can comprise any of a number of devices allowing the mobile device 150 to receive data, such as a keypad 418 (hard or soft), a touch display, voice/speech or motion interfaces, scanners, readers, or other input device. In embodiments including a keypad 418, the keypad 418 can include (or cause display of) the conventional numeric (0-9) and related keys (#, *), and other keys used for operating the mobile device 150 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the mobile device can collect contextual data as part of the telematics data.

The mobile device 150 may also include volatile storage or memory 422 and/or non-volatile storage or memory 424, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the mobile device 150.

In an exemplary embodiment, the mobile device 150 may receive one or more detected gas measurements (e.g., detected EtO measurements, etc.) from the gas detection module 378 of the carrier communication device 110. In this manner, a user (e.g., personnel (e.g., a driver, a loader, a sorter, etc.) of a carrier) of the mobile device 150 may be able to view the received gas measurements via the display 416 of mobile device 150. As such, a user may receive measurements (e.g., gas measurements) regarding a gas level(s) (e.g., EtO level(s)) in a storage space/area (e.g., a trailer) of a vehicle (e.g., vehicle 100 (e.g., a tractor-trailer vehicle)) without the user entering a ventilation system (e.g., ventilation system 70 of FIGS. 6A-6D) and manually obtaining the measurements.

II. Exemplary System Operation

Reference will now be made to example embodiments of a system for efficiently exhausting air from a storage space/area of a vehicle. In this regard, in an example embodiment, a ventilation system is configured to blow air between the top of one or more items (e.g., products, packages, etc.) and a ceiling of the storage space/area (e.g., a trailer). At the front of the storage space/area (e.g., a trailer), the air may slow down, and return to the back of the storage space/area (e.g., a trailer), exhausting one or more gases (e.g., EtO) with the air through one or more exhaust fans, as described more fully below.

Referring now to FIG. 5A and FIG. 5B, an example embodiment of a facility is provided according to an exemplary embodiment of the invention. In one example embodiment, the facility 3 may be a sorting facility in which one or more vehicles of a carrier may transport one or more items (e.g., products, packages, etc.) in route to and from delivery destinations. The facility 3 may have one or more loading docks having lock doors in which one or more vehicles may back up to the dock doors such that a storage space/area (e.g., a trailer) of the vehicles may be accessible via the dock doors. In an example embodiment, one or more of the dock doors of the facility 3 may have a ventilation system (e.g., ventilation system 70 of FIGS. 6A-6D) attached thereto and the vehicles (e.g., vehicles 100) may back up to the ventilation system such that the ventilation system may blow air into the storage space/area (e.g., a trailer) of the vehicle (e.g., vehicle 100) to exhaust one or more gases (e.g., EtO gas) with the air from the storage space/area of the vehicle, as described more fully below. In addition, the facility 3 may supply power to the ventilation system.

Figure 6B:
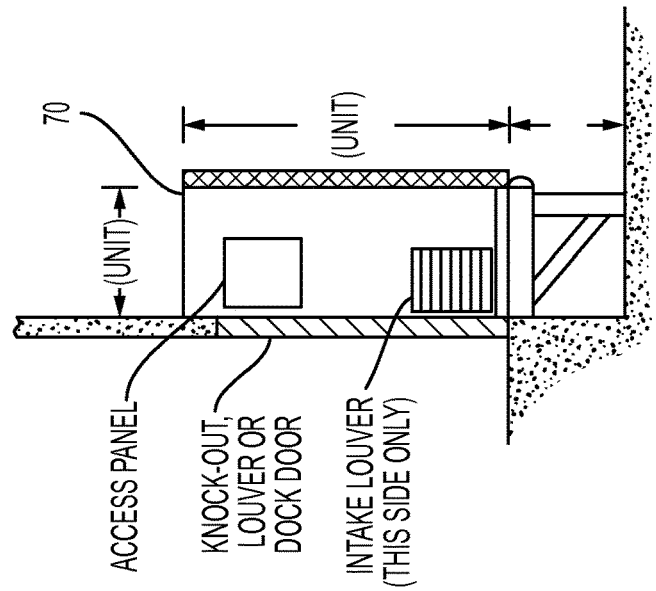
Figure 6A:
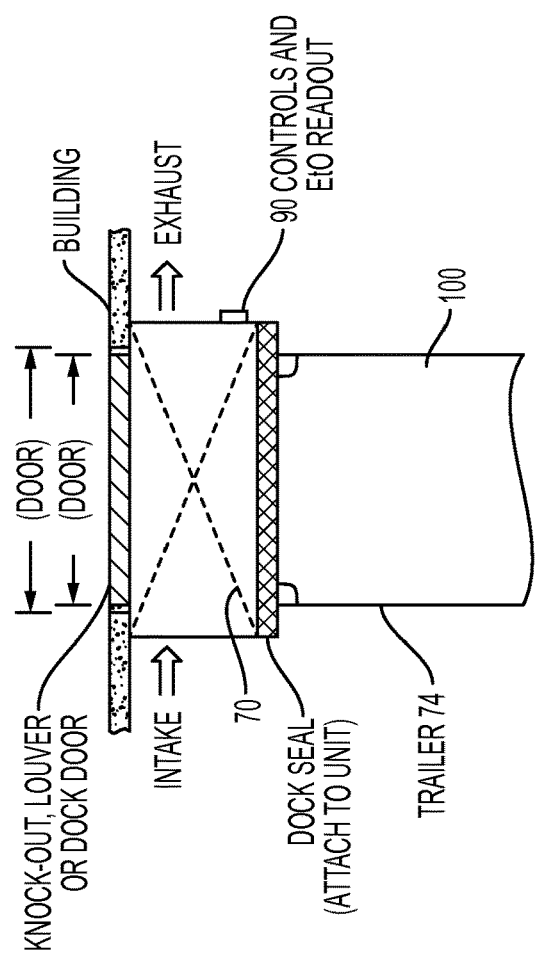
Figure 6D:
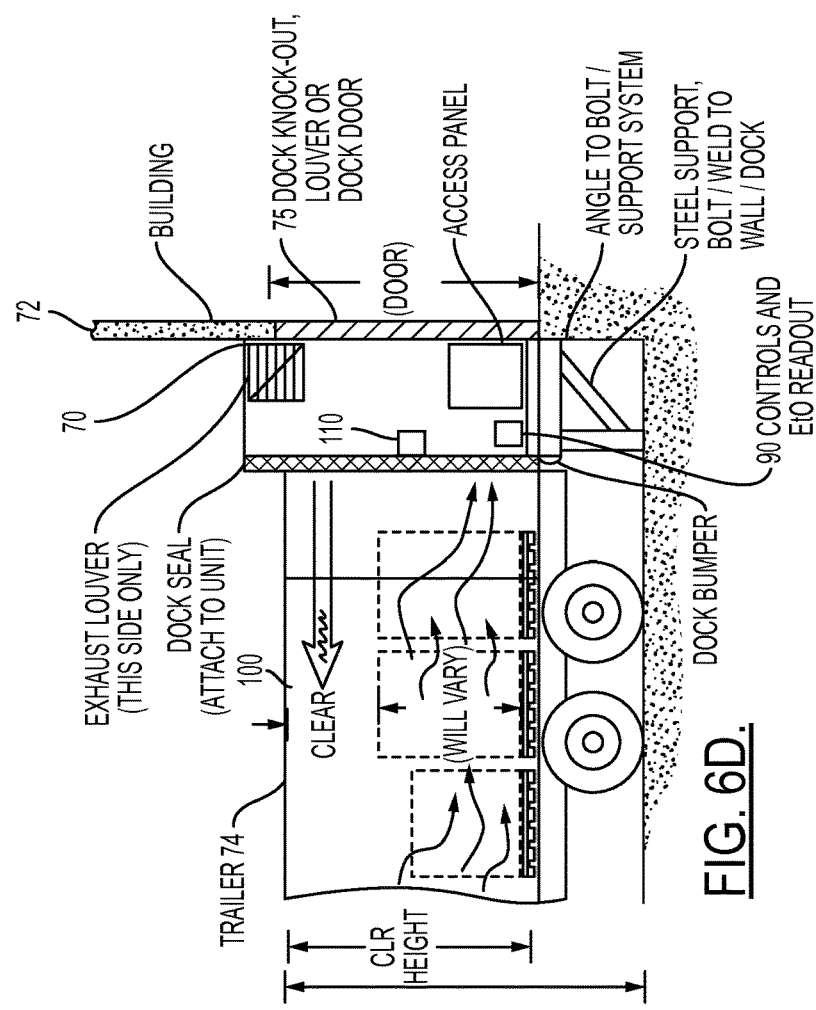
Figure 6C:
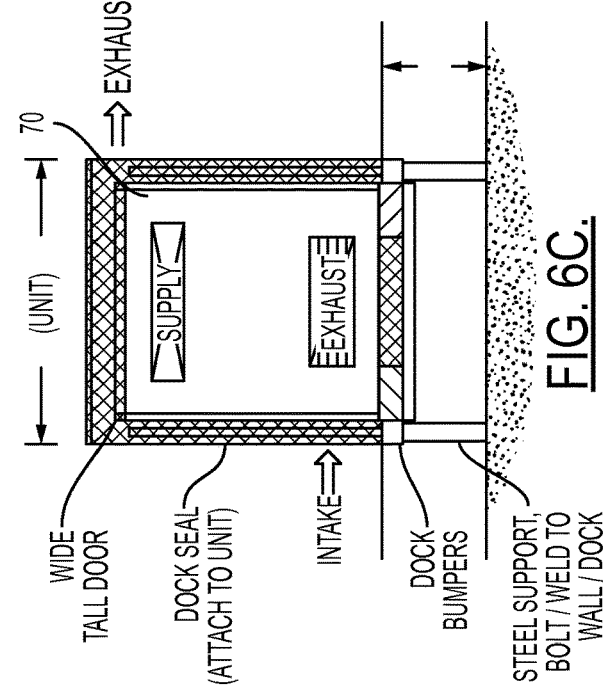

Referring now to FIGS. 6A-6D, diagrams illustrating various perspective views of a ventilation system according to an example embodiment is provided. For instance, FIG. 6A illustrates a top view of a ventilation system 70 (also referred to herein as ventilation unit 70) with a storage space/area (e.g., a trailer 74) of a vehicle (e.g., vehicle 100) backed up to the ventilation system 70 in a facility (e.g., facility 3). FIG. 6B illustrates a side view of the ventilation system 70 in the facility. FIG. 6C illustrates a front view of the ventilation system 70 in a facility. FIG. 6D illustrates a side view of a ventilation system 70 with a storage space/ area (e.g., a trailer) of a vehicle (e.g., vehicle) backed up to the ventilation system 70 and in which ventilation system 70 is mounted to a portion of an exterior side of a dock wall 72 and a dock door 75 (also referred to herein as dock knockout, louver or dock door 75) of a facility. As shown in FIG. 6D, the carrier communication device 110, which includes the gas detection module 378 is also in the ventilation system 70. In addition, FIGS. 6A and 6D also illustrate that the controls and EtO readout device 90 is mounted to a side wall of the ventilation system 70.

Figure 7:
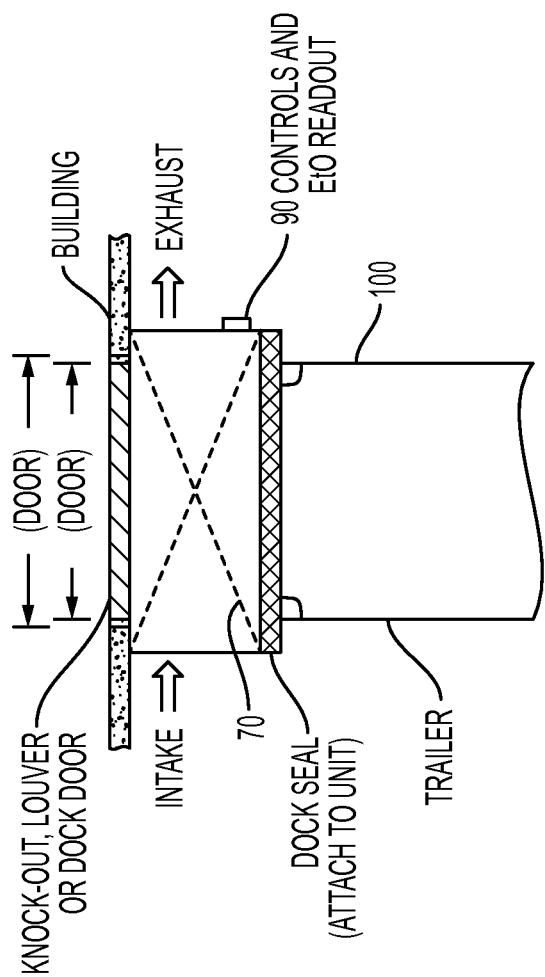

Referring now to FIG. 7, a diagram illustrating a top view of a ventilation system in a facility is provided according to an example embodiment. In this example embodiment, FIG. 7 illustrates that intake air is blown into the storage space/area (e.g., a trailer) of a vehicle (e.g., vehicle 100) and that air is exhausted out of the storage space/area and exits out of the ventilation system 70, as described more fully below.

Figure 8:
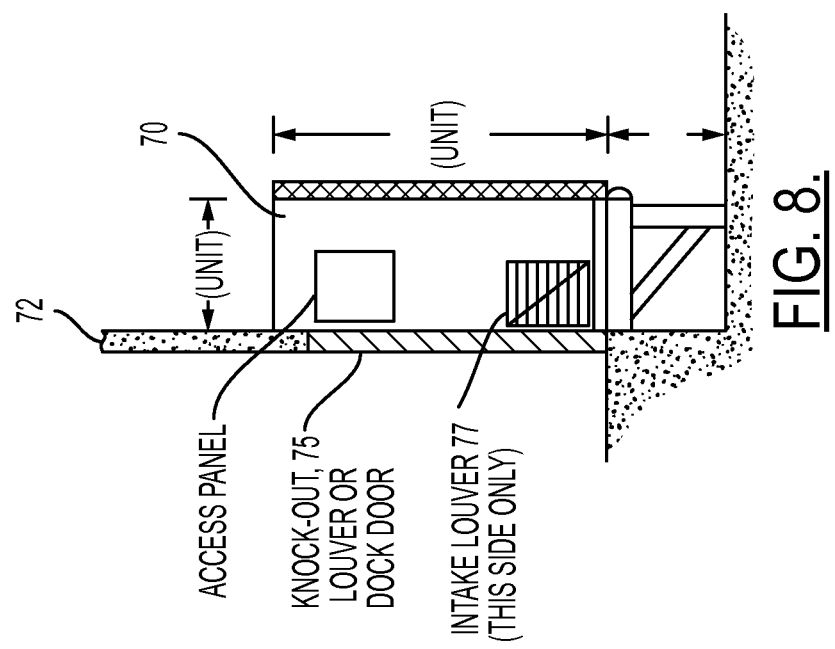

Referring now to FIG. 8, a diagram illustrating a side view of a ventilation system in a facility is provided according to an example embodiment. In this example embodiment, FIG. 8 illustrates that the intake air blown into the storage space/area of the vehicle is protected from escaping from the ventilation system 70 by a louver 77 (also referred to herein as intake louver 77) to keep out, or minimize, rain from entering the ventilation system 70. The louver 77 may also have a filter to keep out, or minimize, debris, insects, etc. from entering the ventilation system 70.

Figure 9:
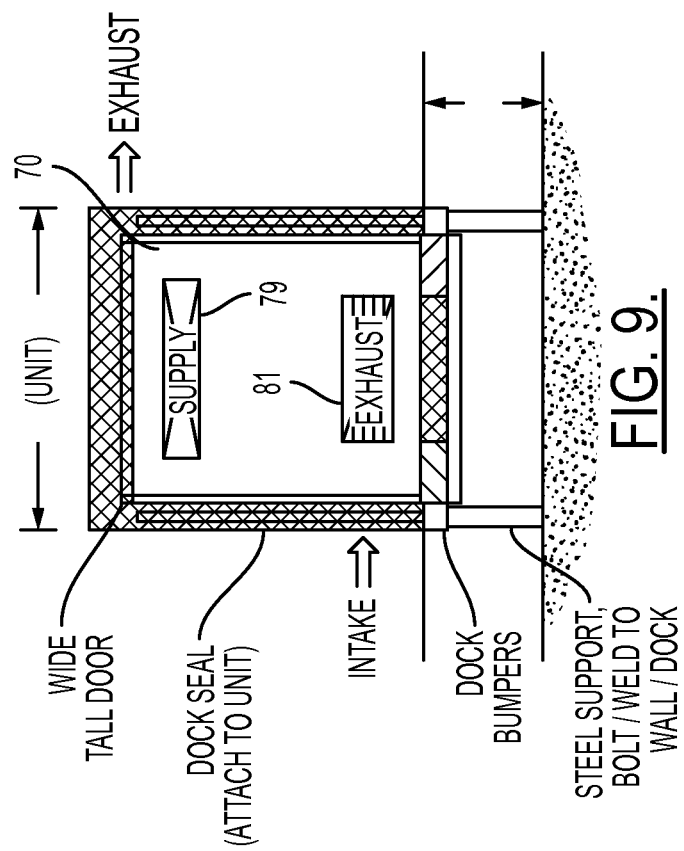

Referring now to FIG. 9, a diagram illustrating a front view of a ventilation system in a facility is provided according to an exemplary embodiment. In the example embodiment of FIG. 9, the supply unit 79 may include one or more first fans/blowers (e.g., a first set of fans/blowers) and the exhaust unit 81 may include one or more second fans/ blowers (e.g., second set of fans/blowers). The supply unit 79 may be located high on the ventilation unit 70 and may blow, via the one or more first fans/blowers (e.g., the first set of fans/blowers), a high-velocity jet of air from the back of the storage space/area (e.g., trailer) to the front of the storage space/area of the vehicle (e.g., vehicle 100). The first fan(s)/blower(s) may be adjustable to accommodate shorter storage space/areas. Adjustment of the first fan(s)/blower(s) of the supply unit 79 may be by variable speed motors. The intake of air (also referred to herein as intake air) may be protected by the louver 77.

In one example embodiment, a heating, ventilating, and air conditioning (HVAC) unit may drive the first fan(s)/blower(s) and the second fan(s)/blower(s). In this regard, the HVAC unit of the first fan(s)/blower(s) and the second fan(s)/blower(s) may target 60 air changes per hour (ACH). In some example embodiments, the ACH may be higher to achieve higher throws of air for longer and/or larger storage space/areas (e.g., a 53 feet long trailer, etc.) to throw/push the air from the back of the storage space/area (e.g., trailer 74) to the front of the storage space/area (e.g., trailer 74) of the vehicle (e.g., vehicle 100).

The exhaust unit 81 including the second one or more fans/blowers (e.g., the second set of fans/blowers) may, but need not, be located lower on the ventilation unit 70 to pull contaminated air out of the storage space/area (e.g., trailer 74) of the vehicle (e.g., vehicle 100). The exhaust unit 81 may have a screen or louver (e.g., louver 76 of FIG. 10) (also referred to herein as exhaust louver 76) in front of the second fan(s)/blower(s) to prevent any large debris (for example, pieces of wood broken off a pallet, etc.) from being drawn into the second fan(s)/blower(s). The exhaust air may exit out of the top of the ventilation unit 70 such as, for example, a duct at a top portion of the ventilation unit 70 that is high enough so that the exhaust air does not mix with the supply air.

Referring now to FIG. 10, a diagram illustrating a side view of a ventilation unit of a facility is provided according to an exemplary embodiment. As shown in FIG. 10, the ventilation unit 70 may be mounted to a portion of an exterior side of a dock wall 72 of a facility (e.g., facility 3) and may, but need not, be approximately the same overall width and height (e.g., 11 feet height (H)×10 feet, 8 inches width (W)) as a dock door 75 or a dock door seal. The ventilation unit 70 may, but need not, protrude approximately 4 feet, 4 inches from the dock wall 72 of the facility. The ventilation unit 70 may be installed on the dock knockout, louver or dock door 75. Additionally, the ventilation unit 70 may have a steel frame capable of supporting all equipment of the ventilation unit 70 and may be strong enough to withstand the impact of a loaded storage space/area (e.g., trailer 54) (e.g., a 53 feet long trailer) of a vehicle (e.g., vehicle 100) backing up to the front of the ventilation unit 70.

In addition, the outside face of the ventilation unit 70 may have a dock seal attached similar to a dock door (e.g., dock door 75). The ventilation unit 70 is configured to withstand 40 pounds per square foot (psf) of pressure in the area that the seal is installed. Furthermore, the ventilation unit 70 may have additional support and bracing underneath the ventilation unit 70. The ventilation unit 70 may be re-locatable. For example, if a facility (e.g., facility 3) were to close, the ventilation unit 70 may be uninstalled and reinstalled (for example, reinstalled to another dock wall and/or dock door of another facility).

The ventilation unit 70 may not allow access to the storage space/area (e.g., trailer 74) of the vehicle (e.g., vehicle 100) from the facility (e.g., facility 3). In an instance in which the ventilation unit 70 is installed on a dock door (e.g., dock door 75), the ventilation unit 70 may block access to any storage space/area (e.g., trailer 74) backed up to the ventilation unit 70. After utilizing the ventilation unit 70 to remove gas (e.g., EtO gas) (or at least remove gas (e.g., EtO gas) to a target level or below) from the storage space/area (e.g., trailer 74) of a vehicle, the storage space/area (e.g., trailer 74) may be moved to another dock door for unloading (e.g., unloading packages, products from the storage space/ area).

The ventilation unit 70 may perform gas monitoring (e.g., EtO monitoring). In this regard, the ventilation unit 70 may include carrier communication device 110 having a gas detection module 378. The gas detection module 378 may continuously or periodically sample the exhaust air to determine the levels of gas (e.g., EtO gas) in the exhaust air while the ventilation unit 70 is in operation.

The gas detection module 378 may utilize these gas measurements (e.g., EtO gas measurements), in part, to provide a user information regarding the gas level (e.g., EtO level) in the storage space/area (e.g., trailer 74) of a vehicle (e.g., vehicle 100). For instance, the gas detection module 378 may provide one or more gas measurements (e.g., EtO measurements) to the controls and EtO readout device 90 (e.g., computing device 90), which may be mounted on a side of the ventilation unit 70 in one example embodiment. In this regard, a user may view and read the detected gas measurements (e.g., EtO gas measurements) from a display (e.g., display 98) of the controls and EtO readout device 90 without entering the ventilation unit 70 or the storage space/area (e.g., trailer 74) of the vehicle (e.g., vehicle 100) and potentially being exposed to the gas (e.g., EtO gas). Additionally or alternatively, the gas detection module 378 may provide one or more gas measurements (e.g., EtO gas measurements) to a mobile device (e.g., mobile device 150) of a user (e.g., personnel of a carrier). In this regard, the gas detection module 378 may provide accurate measurements of gas levels (e.g., EtO levels) and may eliminate the need for an individual (e.g., personnel of a carrier) to enter the storage space/area (e.g., trailer 74) of a vehicle (e.g., vehicle 100) to manually take gas measurements (e.g., EtO measurements).

In preparation of testing the storage space/area (e.g., trailer 74) of a vehicle (e.g., vehicle 100) for one or more gases such as, for example, EtO, the vehicle should be turned off to minimize exhaust contamination of a gas reading (e.g., EtO reading). Additionally or alternatively, in instances in which the storage space/area of the vehicle is removable from the vehicle, the storage space/area (e.g., trailer 74) may be removed or dropped off from the vehicle to minimize exhaust contamination of a gas reading (e.g., EtO reading).

Any storage space/area (e.g., trailer 74) carrying one or more products (e.g., medical devices) that have been sterilized using EtO and/or carrying items (e.g., packages) that include goods (e.g., solvents, antifreeze, textiles, detergents, adhesives, polyurethane foam, pharmaceuticals, fumigants, etc.) that have EtO may be processed utilizing the ventilation unit 70. The storage space/area (e.g., trailer 74) of the vehicle may be opened and backed up to the ventilation unit 70 in a manner similar to backing up to a standard dock door. In an instance in which the ventilation unit 70 is placed (or seated) against a dock seal (e.g., dock seal 83 of FIG. 10) and when the storage space/area (e.g., trailer 74) of the vehicle (e.g., vehicle 100) is secured with chock blocks or a lock, the ventilation unit 70 may be turned on.

For instance, the supply unit 79 having one or more fans/blowers (e.g., a first set of fans/blowers), located high on the ventilation unit 70 may be turned on/activated and may blow air (e.g., a high-velocity jet of air) (e.g., intake air) into the back of the storage space/area (e.g., trailer 74), between the top of one or more items (e.g., items 82, 85, 87) and a ceiling of the storage space/area (e.g., trailer 74), to the front of the storage space/area (e.g., trailer 74). The items (e.g., items 82, 85, 87) may be one or more products (e.g., medical equipment) sterilized with EtO and/or packages having goods (e.g., solvents, antifreeze, textiles, detergents, adhesives, polyurethane foam, pharmaceuticals, fumigants, etc.) that include EtO. In this regard, these items (e.g., items 82, 85, 87) may emit EtO). As described above, the intake air from the one or more fans/blowers of the supply unit 79 may be protected with a louver (e.g., louver 77) to keep out rain and a filter to keep out debris, insects, etc.

The exhaust unit 81 having one or more fans/blowers (e.g., a second set of fans/blowers) located lower on the ventilation unit 70 may pull the air (also referred to herein as exhaust air) (e.g., contaminated air) from the front of the storage space/area (e.g., trailer 74) causing the air to slow down and to return to the back of the storage space/area (e.g., trailer 74). In this regard, the exhaust air may return to the back of the storage space/area (e.g., trailer 74) by moving/traversing between and under other items (e.g., pallets, products, packages, etc.), and thus exhausting the gas (e.g., EtO gas) included in the exhaust air through the one or more fans/blowers of the exhaust unit 81. In this regard, the fans/blowers of the exhaust unit 81 may also cause the exhaust air with the gas to exit out of a top of the ventilation unit 70 via a duct of the ventilation unit 70 that is high enough such that the exhaust air does not mix with the air (e.g., intake air) of the supply unit 79.

As the exhaust air with the gas travels to the back of the storage space/area (e.g., trailer 74) and passes through the lower portion of the ventilation unit 70, the gas detection module 378 of the carrier communication device 110 may detect/measure an amount of gas (e.g., EtO gas) in the exhaust air and may determine a level of the gas (e.g., an EtO level). In addition, the gas detection module 378 may send one or more of the detected gas measurements (e.g., EtO measurements) to the computing device 90 and/or mobile device 150 such that a user (e.g., personnel of a carrier) may view a value(s) of the detected gas measurements (e.g., EtO measurements) via a display (e.g., display 98) of the computing device 90 (e.g., mounted to a side of the ventilation system 70, etc.) or a display (e.g., display 416) of the mobile device 150 and such that the user does not need to enter the ventilation unit 70 or the storage space/area (e.g., trailer 74) of the vehicle (e.g., vehicle 100) to obtain the detected gas measurements (e.g., EtO gas measurements).

In an example embodiment, the gas detection module 378 may continue to detect/measure gas (e.g., EtO gas) from the exhaust air until the gas detection module 378 detects a measurement equal to or below a target level (also referred to herein as a predetermined threshold). In some example embodiments, the target level may be a concentration of 0.5 per million parts of air (ppm) EtO (e.g., calculated as an 8-hour time-weighted average (TWA). In other example embodiments, the target level may be 5 ppm EtO over a 15 minute time period.

In response to detecting that a gas measurement (e.g., an EtO gas measurement) equals or is below the target level, the gas detection module 378 may send a signal(s) to the exhaust unit 81 and the supply unit 79 to deactivate/turn off. As such, the supply unit 79 may turn off the one or more first fans/blowers (e.g., a first set of fans/blowers) in response to receiving the signal(s) and the exhaust unit 81 may turn off the one more second fans/blowers (e.g., a second set of fans/blowers) in response to receiving the signal(s).

In some other alternative example embodiments, in response to detecting that a gas measurement (e.g., an EtO gas measurement) equals or is below the target level, the gas detection module 378 may send a signal(s) to the exhaust unit 81 and the supply unit 79 to continue operation for a predetermined amount of time to maintain a gas level (e.g., EtO level) at the target level or below the target level.

Referring now to FIG. 11, a flowchart of an example method for removing gas from a vehicle storage unit is provided according to an example embodiment. At operation 1100, an apparatus (e.g., ventilation unit 70) may direct or blow a stream of air, from a fan(s) of a supply unit (e.g., supply unit 79) located in an upper part of the apparatus (e.g., ventilation unit 70), into a rear of a vehicle storage space (e.g., trailer 74), between an upper portion of one or more items and a ceiling of the vehicle storage space, to a front of the vehicle storage space. The items (e.g., items 82, 85, 87) may emit at least one gas (e.g., EtO gas).

At operation 1105, the apparatus (e.g., ventilation unit 70) may draw or pull the air including the emitted gas (e.g., EtO gas), via another fan(s) of an exhaust unit (e.g., exhaust unit 81) located in a lower part of the apparatus (e.g., ventilation unit 70), from the front of the vehicle storage space to the rear of the vehicle storage space and through the apparatus (e.g., ventilation unit 70) forcing the air including the emitted gas to exit out of a top portion (e.g., a duct) of the apparatus (e.g., ventilation unit 70).

At operation 1110, the apparatus (e.g., ventilation unit 70) may measure (e.g., via a gas detection sensor 378 disposed proximate the exhaust unit 81) the gas (e.g., EtO gas) as the drawn/pulled air passes through the apparatus (e.g., ventilation unit 70) to determine whether the measured gas equals or is below a predetermined threshold (e.g., 0.5 ppm EtO).

Referring now to FIG. 12, a flowchart of an example method for removing gas from a vehicle storage unit is provided according to another example embodiment. At operation 1200, an apparatus (e.g., carrier communication device 110) may detect air being pulled, via at least one fan (e.g., a second set of fans/blowers) of an exhaust unit (e.g., exhaust unit 81), from the front of a vehicle storage space (e.g., trailer 74) of a vehicle (e.g., vehicle 100) to a rear of the vehicle storage space (e.g., trailer 74) and through a ventilation unit (e.g., ventilation unit 70) forcing the air including at least one emitted gas (e.g., EtO gas) to exit out of a top portion (e.g., a duct) of the ventilation unit.

The air is initially directed or blown, from at least one fan (e.g., a first set of fans/blowers) of a supply unit (e.g., supply unit 79) located in an upper part of the ventilation unit (e.g., ventilation unit 70), into the rear of the vehicle storage space (e.g., trailer 74), between an upper portion of one or more items (e.g., items 82, 85, 87) and a ceiling of the vehicle storage space, to the front of the vehicle storage space, the items (e.g., items 82, 85, 87) emitted the gas.

At operation 1205, the apparatus (e.g., carrier communication device 110) may measure (e.g., via a processor (e.g., gas detection sensor 378 disposed proximate the exhaust unit 81)) the emitted gas as the drawn/pulled air passes through the ventilation unit (e.g., ventilation unit 70) to determine whether the measured gas equals or is below a predetermined threshold (e.g., 0.5 ppm EtO).

It should be pointed out that FIGS. 11 and 12 are flowcharts of a system, method and computer program product according to an example embodiment of the invention. It will be understood that each block of the flowcharts, and combinations of blocks in the flowcharts, can be implemented by various means, such as hardware, firmware, and/or a computer program product including one or more computer program instructions. For example, one or more of the procedures described above may be embodied by computer program instructions. In this regard, in an example embodiment, the computer program instructions which embody the procedures described above are stored by a memory device (e.g., volatile memory 315, non-volatile memory 310, memory 96, volatile memory 422, non-volatile memory 424) and executed by a processor (e.g., processing element 305, gas detection module 378, processor 94, processing element 408). As will be appreciated, any such computer program instructions may be loaded onto a computer or other programmable apparatus (e.g., hardware) to produce a machine, such that the instructions which execute on the computer or other programmable apparatus cause the functions specified in the flowcharts blocks to be implemented. In one embodiment, the computer program instructions are stored in a computer-readable memory that can direct a computer or other programmable apparatus to function in a particular manner, such that the instructions stored in the computer-readable memory produce an article of manufacture including instructions which implement the function(s) specified in the flowcharts blocks. The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowcharts blocks.

Accordingly, blocks of the flowcharts support combinations of means for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

In an example embodiment, an apparatus for performing the methods of FIGS. 11 and 12 above may comprise a processor (e.g., processing element 305, gas detection module 378, processor 94, processing element 408) configured to perform some or each of the operations (1100-1110, 1200-1205) described above. The processor may, for example, be configured to perform the operations (1100-1110, 1200-1205) by performing hardware implemented logical functions, executing stored instructions, or executing algorithms for performing each of the operations. Alternatively, the apparatus may comprise means for performing each of the operations described above. In this regard, according to an example embodiment, examples of means for performing operations (1100-1110, 1200-1205) may comprise, for example, the processing element 305 (e.g., a processor) (e.g., as means for performing any of the operations described above), the gas detection module 378, the processor 94, the processing element 408 and/or a device or circuitry for executing instructions or executing an algorithm for processing information as described above.

III. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for controlling a level of a gas within a vehicle storage space using a ventilation unit comprising a supply unit having a first blower and an exhaust unit having a second blower, the method comprising:

detecting, using a sensor located within the vehicle storage space, that the level of the gas within the vehicle storage space is equal to or exceeds a predetermined threshold;

activating the first blower to generate a stream of air that is directed through an interior of the vehicle storage space;

activating the second blower to draw the air comprising the gas from within the vehicle storage space through the exhaust unit and out of the vehicle storage space;

detecting, using the sensor located within the vehicle storage space, that the level of the gas within the vehicle storage space is below the predetermined threshold; and modifying the operation of the first and second blowers following the detecting that the level of the gas is below the predetermined threshold, wherein the gas comprises Ethylene Oxide gas, and
wherein the predetermined threshold is 0.5 parts per million of Ethylene Oxide gas.

2. The method of claim 1, further comprising:
performing multiple measurements of the level of the gas in the vehicle storage space with the sensor until the sensor detects that the level of the gas is below the predetermined threshold.

3. The method of claim 1, further comprising:
sending a measurement of the Ethylene Oxide gas from the sensor to a communication device to present the measurement of the Ethylene Oxide gas outside of the vehicle storage space.

4. The method of claim 1, wherein modifying the operation of the first and second blowers comprises operating the first and second blowers for a predetermined amount of time after the sensor detects that the level of the gas in the vehicle storage space is below the predetermined threshold.

5. The method of claim 1, wherein modifying the operation of the first and second blowers comprises deactivating the first and second blowers.

6. The method of claim 1, wherein:
the predetermined threshold comprises a numerical predetermined threshold.

7. A system for controlling a level of a gas within a vehicle storage space, the system comprising:
a ventilation unit, comprising:
a supply unit comprising a first blower, and
an exhaust unit comprising a second blower;
a sensor configured to detect the level of the gas within the vehicle storage space;
at least one processor; and
one or more computer-readable media storing computer-executable instructions thereon that, when executed by the at least one processor, perform a method comprising:
determining, from a first reading of the sensor, that the level of the gas within the vehicle storage space is equal to or exceeds a predetermined threshold;
operating the first blower to generate a stream of air that is directed through an interior of the vehicle storage space;
operating the second blower to draw the air comprising the gas from within the vehicle storage space through the exhaust unit and out of the vehicle storage space;
determining, from a second reading of the sensor, that the level of the gas within the vehicle storage space is below the predetermined threshold; and
following the determination that the level of the gas is below the predetermined threshold, modifying the operation of the first and second blowers,
wherein the gas comprises Ethylene Oxide gas,
wherein the sensor is configured to detect a parts-per-million of the Ethylene Oxide gas in the vehicle storage space, and
wherein the predetermined threshold is 0.5 parts per million.

8. The system of claim 7, wherein the method further comprises:
performing multiple measurements of the level of the gas in the vehicle storage space with the sensor until the sensor indicates that the level of the gas is below the predetermined threshold.

9. The system of claim 7, wherein the method further comprises:
sending a measured level of the Ethylene Oxide gas from the sensor to a communication device to present the measured level of the Ethylene Oxide gas outside of the vehicle storage space.

10. The system of claim 7, wherein modifying the operation of the first and second blowers comprises operating the first and second blowers for a predetermined amount of time after the sensor indicates that the level of the gas is below the predetermined threshold.

11. The system of claim 7, further comprising a dock seal coupled to the ventilation unit, wherein the dock seal is configured to engage with an opening of the vehicle storage space.

12. The system of claim 7, wherein:
the predetermined threshold comprises a numerical predetermined threshold.

13. A ventilation unit for controlling a level of a gas within a vehicle storage space, the ventilation unit comprising:
a sensor configured to detect if the level of the gas within the vehicle storage space is equal to or exceeds a predetermined threshold;
a supply unit comprising a first blower, the supply unit configured to direct a stream of air through the vehicle storage space when the first blower is activated; and
an exhaust unit comprising a second blower, the exhaust unit configured to draw the air comprising the gas through the ventilation unit when the second blower is activated, forcing the air and the gas out of the vehicle storage space,
wherein the ventilation unit is configured to modify, following a detection by the sensor that the level of the gas within the vehicle storage space is equal to or exceeds the predetermined threshold, the operation of the first and second blowers,
wherein the gas comprises Ethylene Oxide gas, and
wherein the predetermined threshold is 0.5 parts per million of the Ethylene Oxide Gas.

14. The ventilation unit of claim 13, wherein the ventilation unit is further configured to:
perform multiple measurements of the level of the gas in the vehicle storage space using the sensor until the sensor detects that the level of the gas is below the predetermined threshold.

15. The ventilation unit of claim 13, wherein the ventilation unit is configured to:
send a measurement of the level of the Ethylene Oxide gas from the sensor to a communication device.

16. The ventilation unit of claim 13, wherein modifying the operation of the first and second blowers comprises operating the first and second blowers until the sensor detects that the level of the gas within the vehicle storage space is below the predetermined threshold.

17. The ventilation unit of claim 13, wherein the level of the gas is detected in parts per million by the sensor.

18. The ventilation unit of claim 13, wherein:
the predetermined threshold comprises a numerical predetermined threshold.

* * * * *

UNITED STATES PATENT AND TRADEMARK OFFICE
CERTIFICATE OF CORRECTION

PATENT NO. : 10,377,206 B2
APPLICATION NO. : 14/626059
DATED : August 13, 2019
INVENTOR(S) : Michael Patrick Kehoe et al.

Page 1 of 1

It is certified that error appears in the above-identified patent and that said Letters Patent is hereby corrected as shown below:

In the Specification

Column 01, Line 57: Please remove "gas(es))" and replace with --gas(es)--.
Column 07, Line 33: Please remove "sulfer" and replace with --sulfur--.

Signed and Sealed this
Eighth Day of October, 2019

Andrei Iancu
*Director of the United States Patent and Trademark Office*